(12) United States Patent
Shelton, IV

(10) Patent No.: US 9,289,207 B2
(45) Date of Patent: Mar. 22, 2016

(54) SURGICAL STAPLE WITH INTEGRAL PLEDGET FOR TIP DEFLECTION

(71) Applicant: Ethicon Endo-Surgery, Inc., Cincinnati, OH (US)

(72) Inventor: Frederick E. Shelton, IV, Hillsboro, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 603 days.

(21) Appl. No.: 13/688,951

(22) Filed: Nov. 29, 2012

(65) Prior Publication Data

US 2014/0144968 A1    May 29, 2014

(51) Int. Cl.
| | |
|---|---|
| A61B 17/04 | (2006.01) |
| A61B 17/10 | (2006.01) |
| A61B 17/068 | (2006.01) |
| A61B 17/064 | (2006.01) |
| A61B 17/072 | (2006.01) |
| A61B 17/11 | (2006.01) |
| A61B 17/115 | (2006.01) |
| A61B 17/00 | (2006.01) |

(52) U.S. Cl.
CPC ......... *A61B 17/0682* (2013.01); *A61B 17/0644* (2013.01); *A61B 17/07292* (2013.01); *A61B 17/1114* (2013.01); *A61B 17/1155* (2013.01); *A61B 2017/00274* (2013.01); *A61B 2017/00473* (2013.01); *A61B 2017/00818* (2013.01); *A61B 2017/0645* (2013.01); *A61B 2017/0725* (2013.01); *A61B 2017/07264* (2013.01); *A61B 2017/1132* (2013.01)

(58) Field of Classification Search
CPC ..................... A61B 17/07292; A61B 17/1155; A61B 17/064; A61B 2017/0726; A61B 7/0682
USPC ................... 227/175.1–182.1; 606/142–143, 606/219–221

See application file for complete search history.

(56) References Cited

U.S. PATENT DOCUMENTS

| | | | | |
|---|---|---|---|---|
| 4,340,331 A | * | 7/1982 | Savino | 411/457 |
| 4,428,376 A | * | 1/1984 | Mericle | 606/219 |
| 4,467,805 A | * | 8/1984 | Fukuda | A61B 17/0644 606/217 |
| 4,485,816 A | * | 12/1984 | Krumme | A61B 17/0644 219/201 |
| 4,531,522 A | * | 7/1985 | Bedi | A61B 17/0644 606/220 |
| 4,548,202 A | * | 10/1985 | Duncan | 606/220 |

(Continued)

FOREIGN PATENT DOCUMENTS

EP    0552433    7/1993

OTHER PUBLICATIONS

International Search Report dated Mar. 27, 2014 for Application No. PCT/US2013/071617.

*Primary Examiner* — Robert Long
(74) *Attorney, Agent, or Firm* — Frost Brown Todd LLC

(57) ABSTRACT

A circular stapler apparatus for stapling tissue includes a staple and pledget assembly and a circular staple head operable to drive staples toward an anvil. A staple of the staple and pledget assembly has a pair of legs disposed substantially perpendicular to a crown of the staple in a first position. The pair of legs is operable to advance against a pocket in the anvil to form a staple with bent legs. The staple and pledget assembly includes the staple and a pledget configured to receive the pair of legs of the staple. The pledget comprises a bioabsorbable material. The pledget is configured to advance distal ends of the pair of legs to a position in which the distal ends are laterally offset from a plane in which the crown of the staple is disposed.

20 Claims, 13 Drawing Sheets

(56) References Cited

U.S. PATENT DOCUMENTS

| | | | |
|---|---|---|---|
| 4,566,621 A * | 1/1986 | Becht ........................... 227/109 |
| 4,632,290 A * | 12/1986 | Green et al. .................... 227/19 |
| 4,805,823 A | 2/1989 | Rothfuss |
| 4,887,601 A * | 12/1989 | Richards ............ A61B 17/0644 411/457 |
| 5,026,390 A * | 6/1991 | Brown ................. A61B 17/083 411/457 |
| 5,205,459 A | 4/1993 | Brinkerhoff et al. |
| 5,209,756 A * | 5/1993 | Seedhom ........... A61B 17/0642 606/151 |
| 5,242,457 A * | 9/1993 | Akopov ............... A61B 17/064 222/175.1 |
| 5,258,009 A * | 11/1993 | Conners ........................ 606/219 |
| 5,271,544 A | 12/1993 | Fox et al. |
| 5,275,322 A | 1/1994 | Brinkerhoff et al. |
| 5,285,945 A | 2/1994 | Brinkerhoff et al. |
| 5,292,053 A | 3/1994 | Bilotti et al. |
| 5,333,773 A | 8/1994 | Main et al. |
| 5,350,104 A | 9/1994 | Main et al. |
| 5,350,400 A * | 9/1994 | Esposito et al. ............... 606/219 |
| 5,415,334 A | 5/1995 | Williamson, IV et al. |
| 5,465,895 A | 11/1995 | Knodel et al. |
| 5,486,187 A * | 1/1996 | Schenck ................. A61B 17/11 606/151 |
| 5,489,058 A * | 2/1996 | Plyley .................. A61B 17/064 227/176.1 |
| 5,533,661 A | 7/1996 | Main et al. |
| 5,597,107 A | 1/1997 | Knodel et al. |
| 5,632,432 A | 5/1997 | Schulze et al. |
| 5,638,582 A * | 6/1997 | Klatt et al. .................... 24/33 P |
| 5,673,840 A | 10/1997 | Schulze et al. |
| 5,704,534 A | 1/1998 | Huitema et al. |
| 5,738,474 A * | 4/1998 | Blewett ............ A61B 17/07207 411/473 |
| 5,785,713 A * | 7/1998 | Jobe .................. A61B 17/0401 606/101 |
| 5,814,055 A | 9/1998 | Knodel et al. |
| 5,843,126 A * | 12/1998 | Jameel ......................... 606/220 |
| 5,947,999 A * | 9/1999 | Groiso ............... A61B 17/0642 606/216 |
| 6,110,187 A * | 8/2000 | Donlon ........................ 606/151 |
| 6,783,524 B2 | 8/2004 | Anderson et al. |
| 6,978,921 B2 | 12/2005 | Shelton, IV et al. |
| 7,000,818 B2 | 2/2006 | Shelton, IV et al. |
| 7,143,923 B2 | 12/2006 | Shelton, IV et al. |
| 7,303,108 B2 | 12/2007 | Shelton, IV |
| 7,367,485 B2 | 5/2008 | Shelton, IV et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,434,715 B2 | 10/2008 | Shelton, IV et al. |
| 7,721,930 B2 | 5/2010 | McKenna et al. |
| 7,959,053 B2 * | 6/2011 | Yasuda ............... A61B 17/0644 227/175.1 |
| 8,186,556 B2 * | 5/2012 | Viola ......................... 227/178.1 |
| 8,231,041 B2 * | 7/2012 | Marczyk et al. ........... 227/178.1 |
| 8,308,041 B2 * | 11/2012 | Kostrzewski .... A61B 17/07207 227/175.1 |
| 8,348,972 B2 * | 1/2013 | Soltz .................. A61B 17/0644 227/175.1 |
| 8,381,961 B2 | 2/2013 | Holsten et al. |
| 8,453,908 B2 * | 6/2013 | Bedi .................. A61B 17/0644 227/176.1 |
| 8,636,191 B2 * | 1/2014 | Meagher ............ A61B 17/0644 227/179.1 |
| 8,720,766 B2 * | 5/2014 | Hess .................. A61B 17/0644 227/175.1 |
| 8,721,646 B2 * | 5/2014 | Fox .................... A61B 17/0642 606/75 |
| 8,727,197 B2 * | 5/2014 | Hess ......................... 227/176.1 |
| 8,808,325 B2 * | 8/2014 | Hess et al. ..................... 606/219 |
| 8,998,061 B2 * | 4/2015 | Williams ........... A61B 17/0644 227/176.1 |
| 2002/0029044 A1 * | 3/2002 | Monassevitch .... A61B 17/0642 606/75 |
| 2002/0190093 A1 * | 12/2002 | Fenton, Jr. .................. 227/176.1 |
| 2004/0006372 A1 * | 1/2004 | Racenet et al. ................ 606/219 |
| 2004/0028502 A1 * | 2/2004 | Cummins ..................... 411/457 |
| 2004/0093024 A1 * | 5/2004 | Lousararian et al. ......... 606/213 |
| 2005/0256537 A1 * | 11/2005 | Cummins et al. ............. 606/219 |
| 2006/0100649 A1 * | 5/2006 | Hart ............................. 606/157 |
| 2006/0278679 A1 * | 12/2006 | Viola et al. .................... 227/155 |
| 2008/0078808 A1 * | 4/2008 | Hess ................. A61B 17/0644 227/181.1 |
| 2009/0255978 A1 * | 10/2009 | Viola et al. ................. 227/180.1 |
| 2010/0187285 A1 * | 7/2010 | Harris et al. ................ 227/175.1 |
| 2010/0217314 A1 * | 8/2010 | Holsten et al. ................ 606/220 |
| 2011/0042439 A1 * | 2/2011 | Johnson et al. ............. 227/175.1 |
| 2011/0060363 A1 * | 3/2011 | Hess et al. .................... 606/219 |
| 2011/0087276 A1 * | 4/2011 | Bedi et al. .................... 606/219 |
| 2011/0226837 A1 * | 9/2011 | Baxter et al. ............... 227/175.1 |
| 2012/0080335 A1 | 4/2012 | Shelton, IV et al. |
| 2012/0193398 A1 * | 8/2012 | Williams et al. ............ 227/179.1 |
| 2012/0248169 A1 * | 10/2012 | Widenhouse et al. ..... 227/175.1 |
| 2013/0168431 A1 * | 7/2013 | Zemlok et al. ............. 227/175.1 |
| 2014/0158747 A1 * | 6/2014 | Measamer et al. ......... 227/179.1 |

* cited by examiner

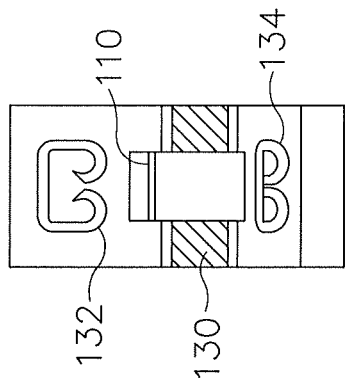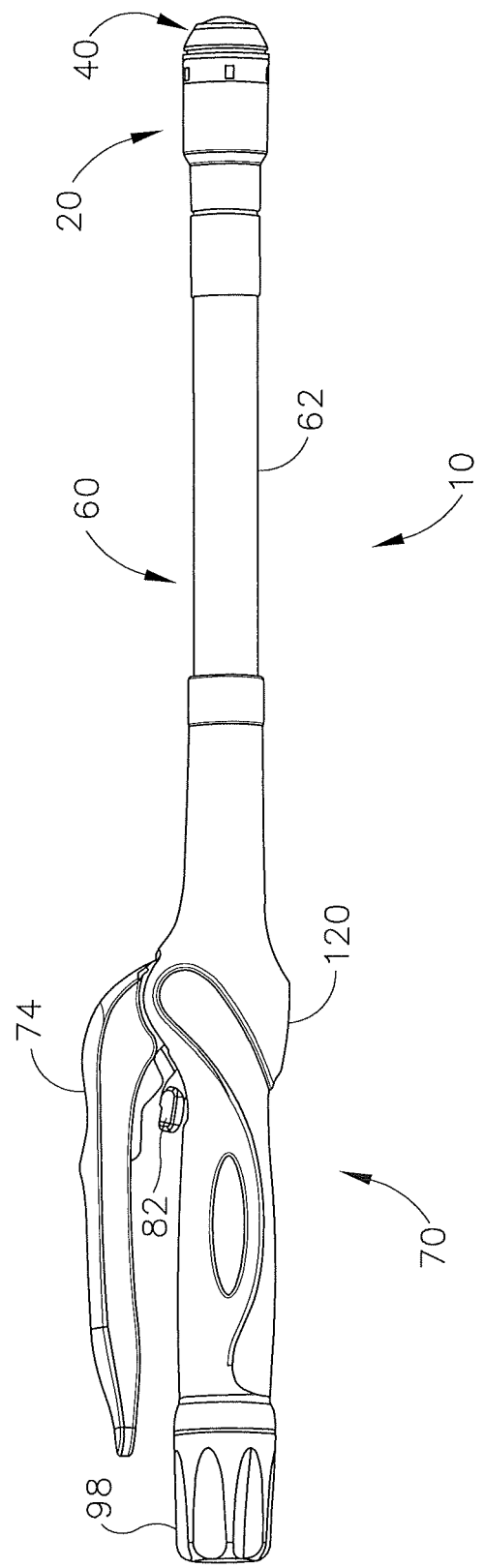

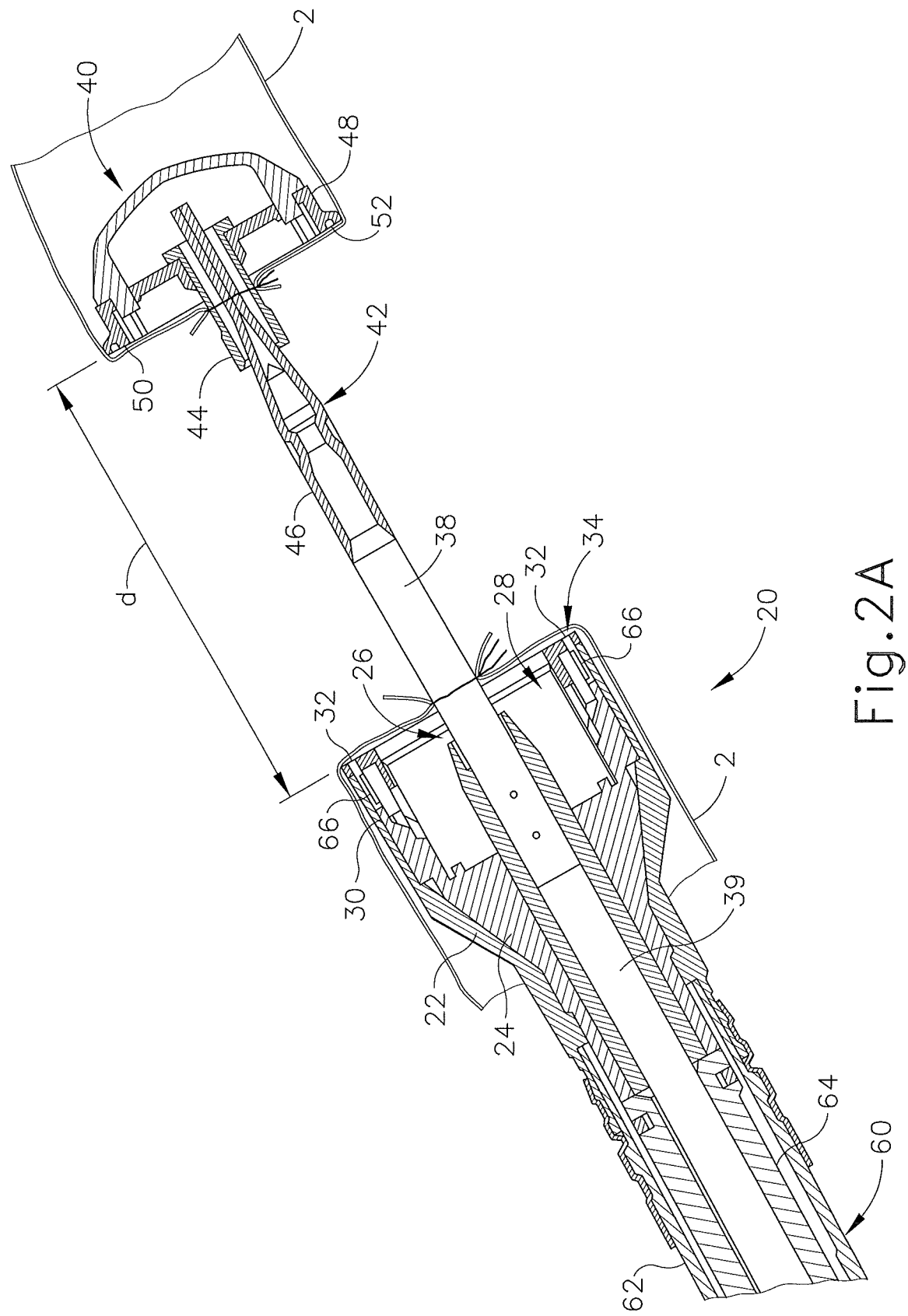

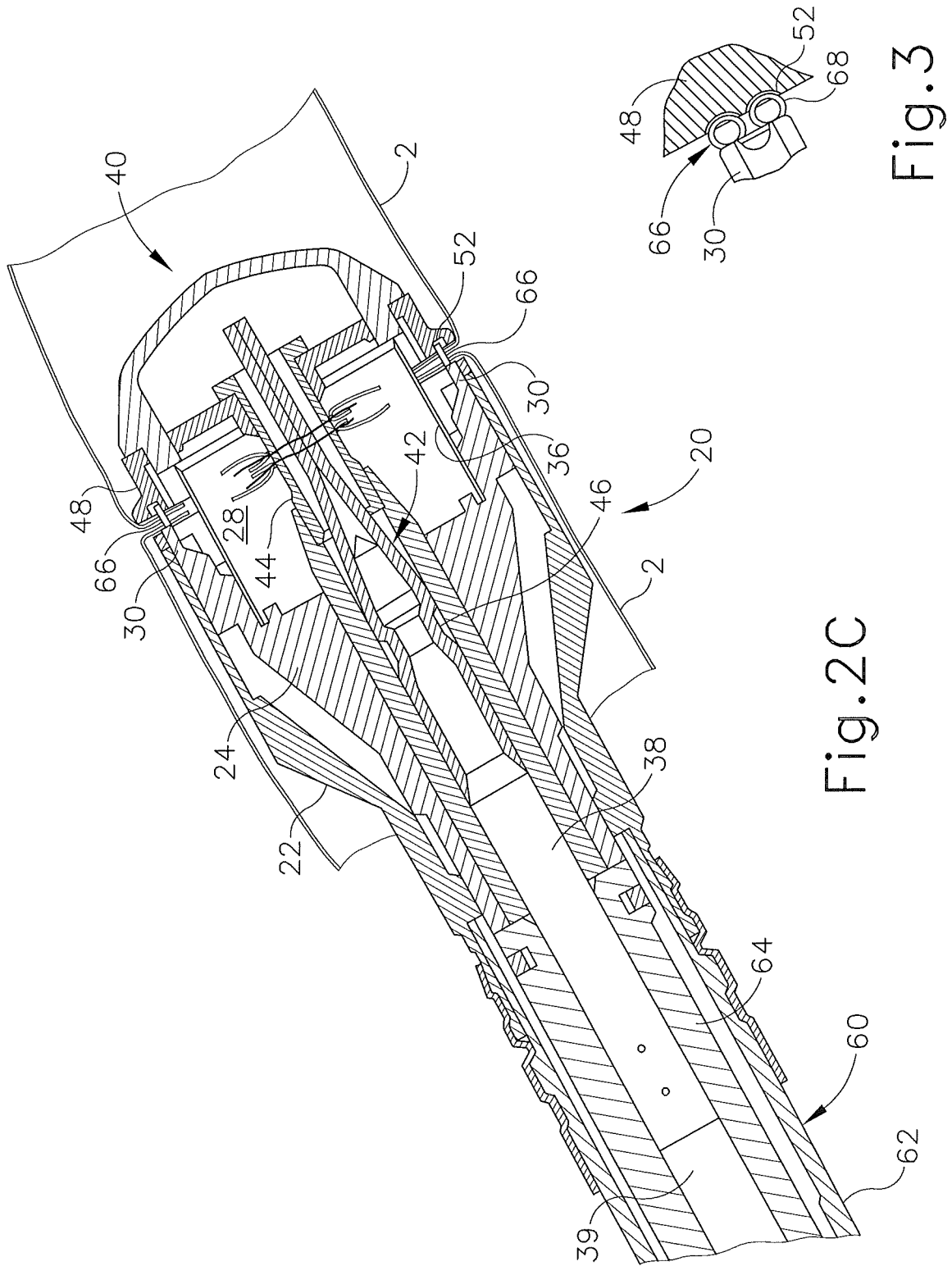

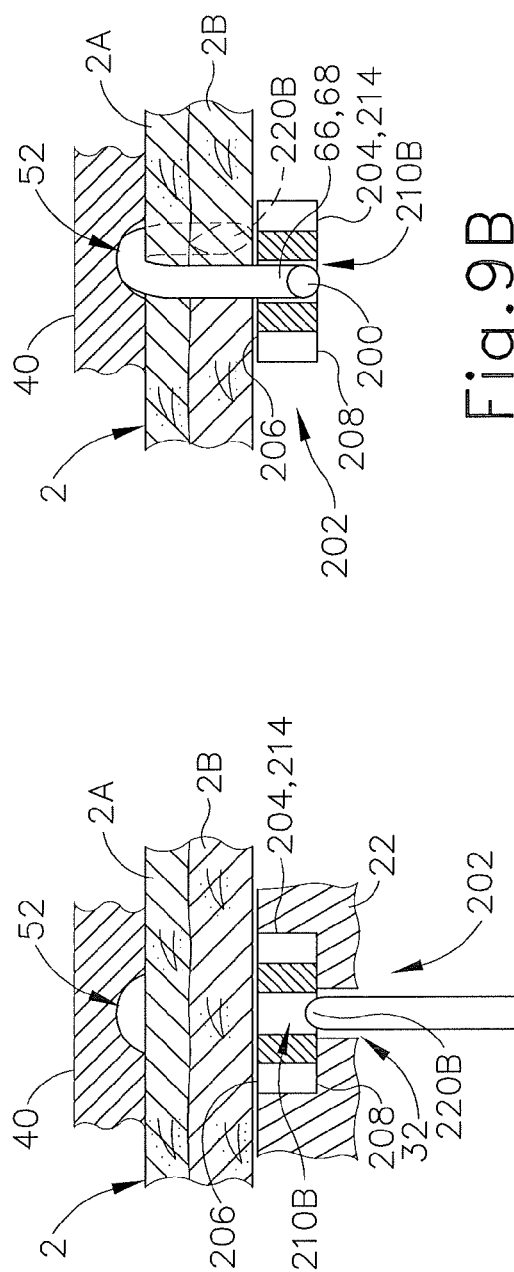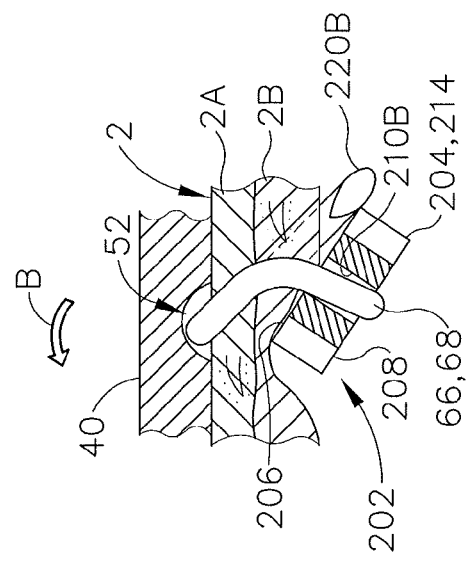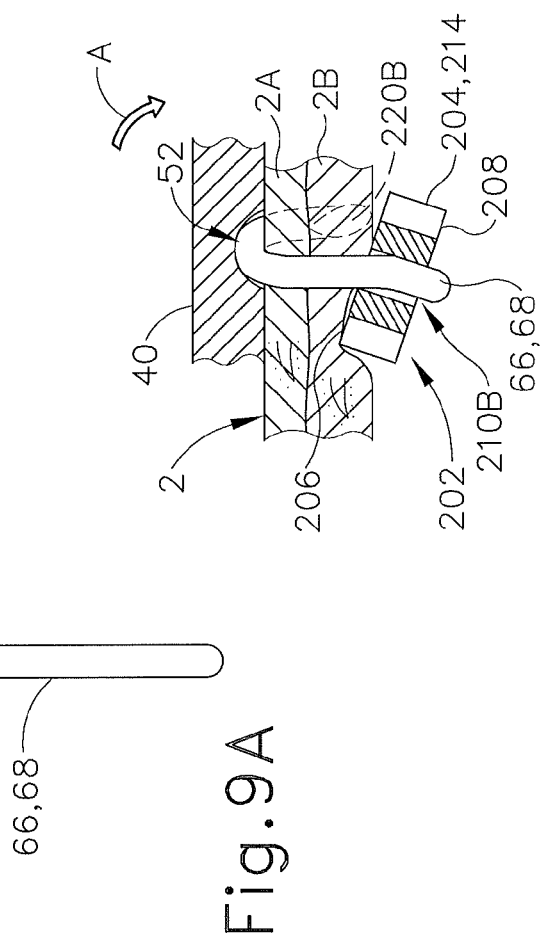

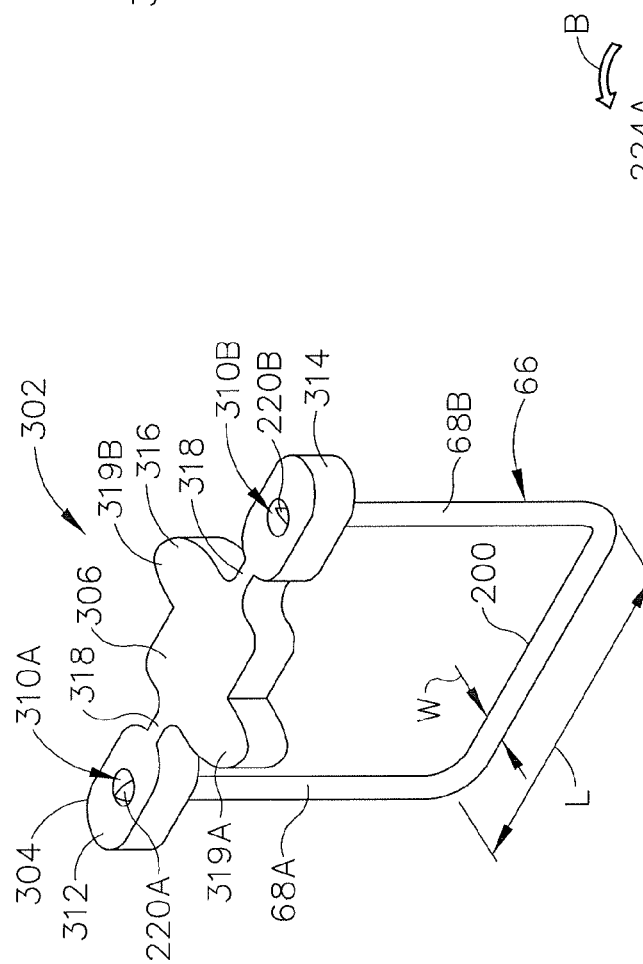
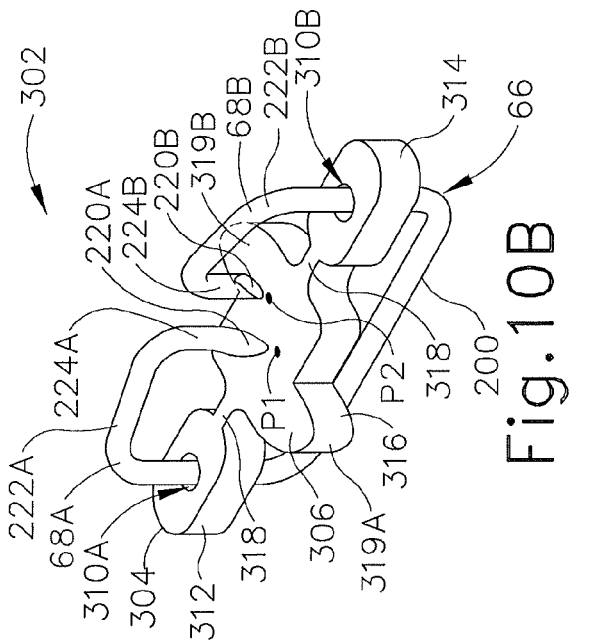
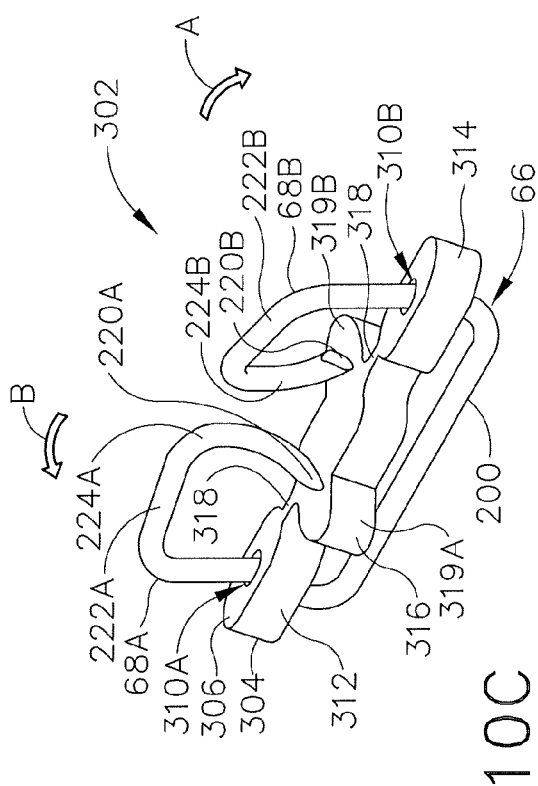

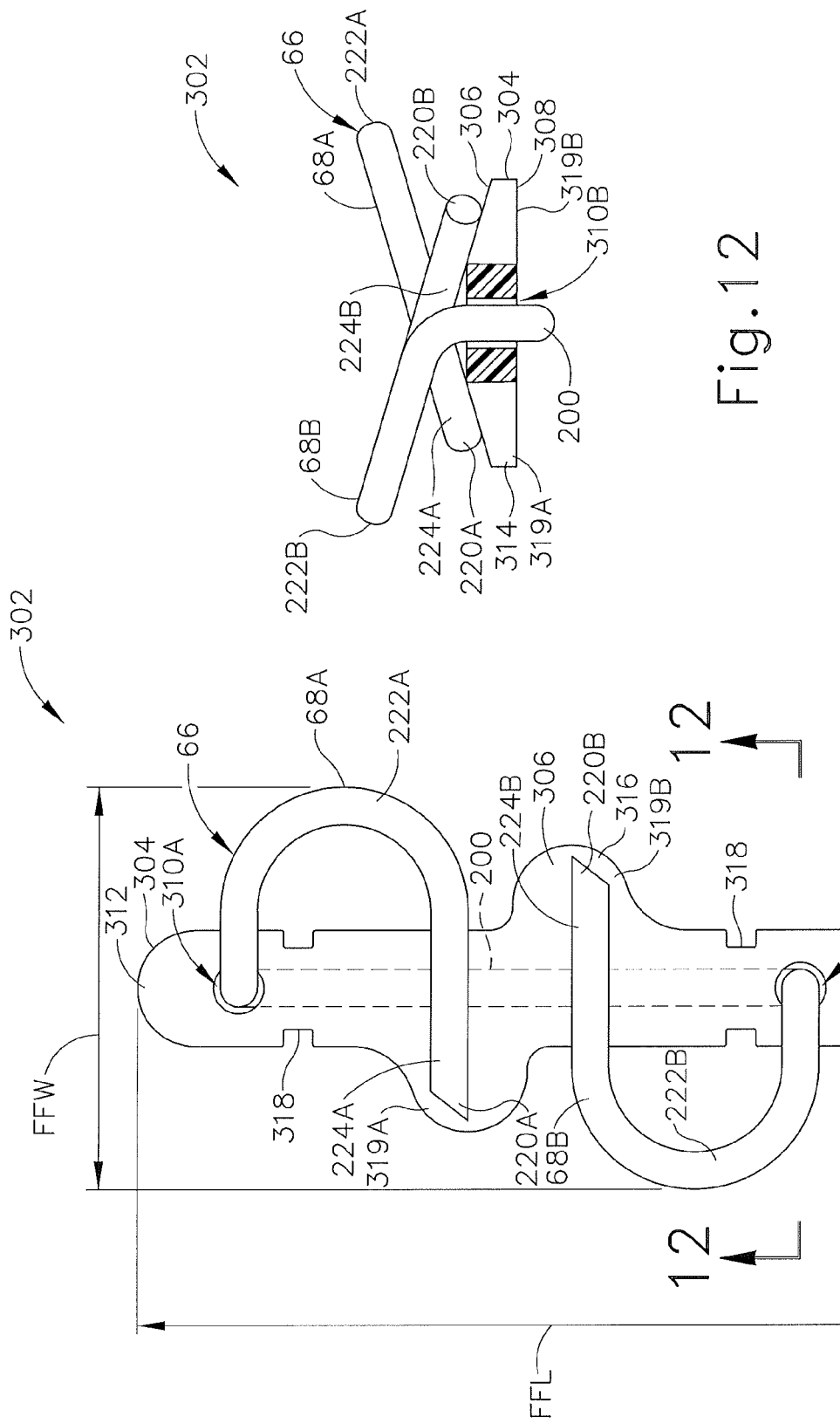

SURGICAL STAPLE WITH INTEGRAL PLEDGET FOR TIP DEFLECTION

BACKGROUND

In some settings, a surgeon may want to position a surgical instrument through an orifice of the patient and use the instrument to adjust, position, attach, and/or otherwise interact with tissue within the patient. For instance, in some surgical procedures, portions of the gastrointestinal tract may be cut and removed to eliminate undesirable tissue or for other reasons. Once the desired tissue is removed, the remaining portions may need to be recoupled together. One such tool for accomplishing these anastomotic procedures is a circular stapler that is inserted through a patient's orifice.

Examples of circular surgical staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996. The disclosure of each of the above-cited U.S. Patents is incorporated by reference herein. Some such staplers are operable to clamp down on layers of tissue, cut through the clamped layers of tissue, and drive staples through the layers of tissue to substantially seal the severed layers of tissue together near the severed ends of the tissue layers, thereby joining two severed ends of an anatomical lumen.

Merely additional other exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; and U.S. Pat. No. 7,721,930, entitled "Disposable Cartridge with Adhesive for Use with a Stapling Device," issued May 25, 2010. The disclosure of each of the above-cited U.S. Patents is incorporated by reference herein. While the surgical staplers referred to above are described as being used in endoscopic procedures, it should be understood that such surgical staplers may also be used in open procedures and/or other non-endoscopic procedures.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 1 depicts a side elevation view of an exemplary circular stapling surgical instrument;

FIG. 2A depicts an enlarged longitudinal cross-section view of an exemplary stapling head assembly of the instrument of FIG. 1 showing an exemplary anvil in an open position;

FIG. 2C depicts an enlarged longitudinal cross-sectional view of the stapling head assembly of FIG. 2A showing an exemplary staple driver and blade in a fired position;

FIG. 3 depicts an enlarged partial cross-sectional view of an exemplary staple formed against the anvil;

FIG. 6 depicts an diagrammatic view of the indicator window of FIG. 5 showing an exemplary indicator bar and exemplary corresponding staple representations;

FIG. 9A depicts a cross-sectional side view of an exemplary staple pocket, an exemplary anvil pocket, tissue disposed between the pockets, and the exemplary staple and pledget assembly of FIG. 7A in the first position;

FIG. 9B depicts a cross-sectional side view of the exemplary anvil pocket, tissue, and the exemplary staple and pledget assembly of FIG. 9A in the second position of FIG. 7B;

FIG. 9C depicts a cross-sectional side view of the exemplary anvil pocket, tissue, and the exemplary staple and pledget assembly of FIG. 9A in the third position of FIG. 7C;

FIG. 9D depicts a cross-sectional side view of the exemplary anvil pocket, tissue, and the exemplary staple and pledget assembly of FIG. 9A in the fourth position of FIG. 7D;

FIG. 10A depicts a perspective view of an exemplary staple in a first position with respect to another exemplary pledget to form another exemplary staple and pledget assembly;

FIG. 10B depicts a perspective view of the exemplary staple and pledget assembly of FIG. 10A in a second position;

FIG. 10C depicts a perspective view of the exemplary staple and pledget assembly of FIG. 10A in a third position;

FIG. 11 depicts an end view of the exemplary staple and pledget assembly of FIG. 10A in a fourth position; and FIG. 12 depicts a cross-sectional side view taken along line 12-12 of FIG. 11.

Figure 2B:
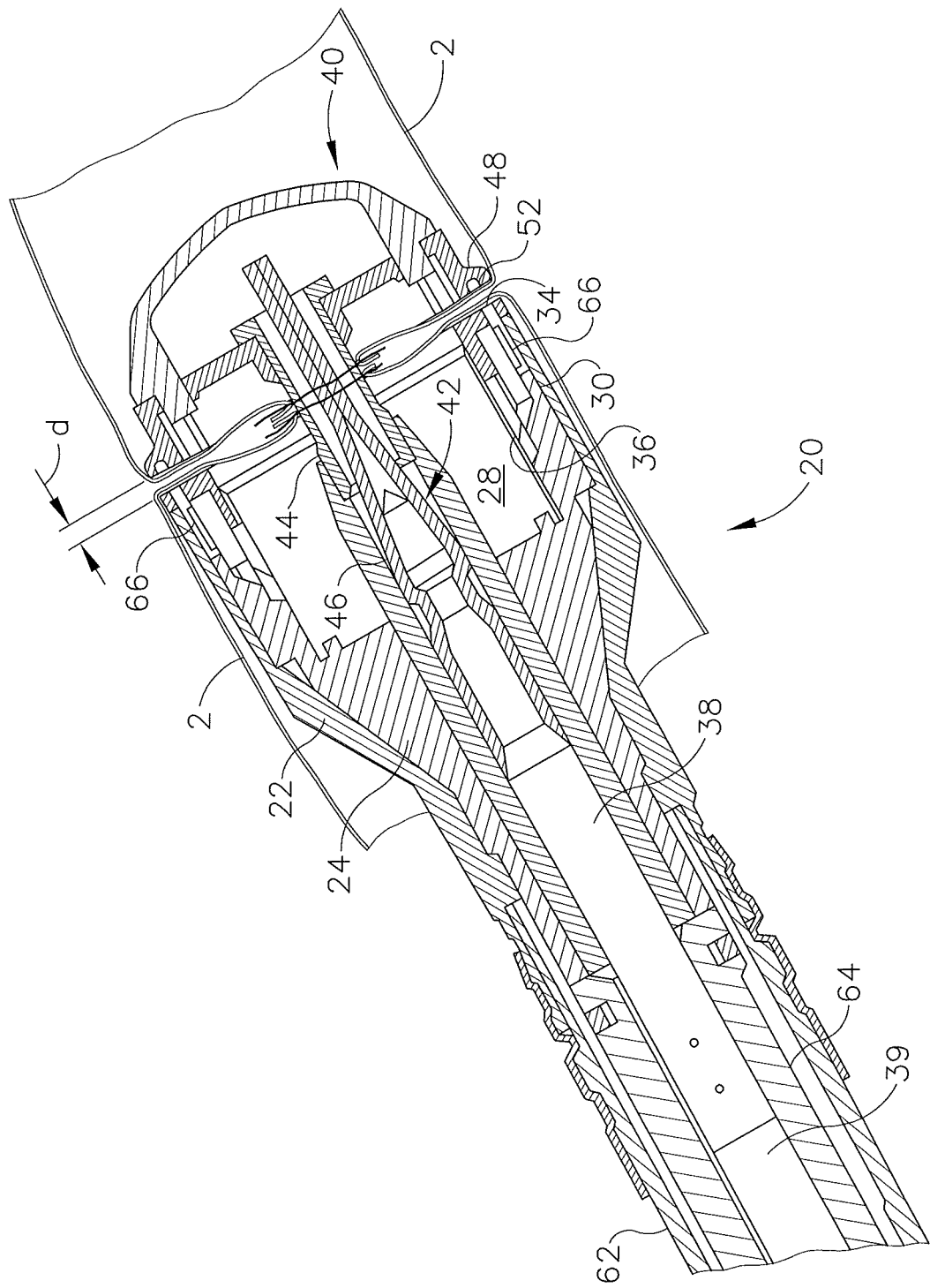
FIG. 2B depicts an enlarged longitudinal cross-sectional view of the stapling head assembly of FIG. 2A showing the anvil in a closed position.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Circular Stapling Surgical Instrument

FIGS. 1-6 depict an exemplary circular surgical stapling instrument (10) having a stapling head assembly (20), a shaft assembly (60), and an actuator handle assembly (70), each of which will be described in more detail below. Shaft assembly (60) extends distally from actuator handle assembly (70) and stapling head assembly (20) is coupled to a distal end of shaft assembly (60). In brief, actuator handle assembly (70) is operable to actuate a staple driver (24) of stapling head assembly (20) to drive a plurality of staples (66) out of stapling head assembly (20). Staples (66) are bent to form completed staples by an anvil (40) that is attached at the distal end of instrument (10). Accordingly, tissue (2), shown in FIGS. 2A-2C, may be stapled utilizing instrument (10).

In the present example, instrument (10) comprises a closure system and a firing system. The closure system comprises a trocar (38), a trocar actuator (39), and a rotating knob (98). An anvil (40) may be coupled to a distal end of trocar (38). Rotating knob (98) is operable to longitudinally translate trocar (38) relative to stapling head assembly (20), thereby translating anvil (40) when anvil (40) is coupled to trocar (38), to clamp tissue between anvil (40) and stapling head assembly (20). The firing system comprises a trigger (74), a trigger actuation assembly (84), a driver actuator (64), and a staple driver (24). Staple driver (24) includes a knife (36) configured to sever tissue when staple driver (24) is actuated longitudinally. In addition, staples (66) are positioned distal to a plurality of staple driving members (30) of staple driver (24) such that staple driver (24) also drives staples (66) distally when staple driver (24) is actuated longitudinally. Thus, when trigger (74) is actuated and trigger actuation assembly (84) actuates staple driver (24) via driver actuator (64), knife (36) and members (30) substantially simultaneously sever tissue (2) and drive staples (66) distally relative to stapling head assembly (20) into tissue. The components and functionalities of the closure system and firing system will now be described in greater detail.

A. Exemplary Anvil

As shown in FIGS. 1-2C, anvil (40) is selectively coupleable to instrument (10) to provide a surface against which staples (66) may be bent to staple material contained between stapling head assembly (20) and anvil (40). Anvil (40) of the present example is selectively coupleable to a trocar or pointed rod (38) that extends distally relative to stapling head assembly (20). Referring to FIGS. 2A-2C, anvil (40) is selectively coupleable via the coupling of a proximal shaft (42) of anvil (40) to a distal tip of trocar (38). Anvil (40) comprises a generally circular anvil head (48) and a proximal shaft (42) extending proximally from anvil head (48). In the example shown, proximal shaft (42) comprises a tubular member (44) having resiliently biased retaining clips (46) to selectively couple anvil (40) to trocar (38), though this is merely optional, and it should be understood that other retention features for coupling anvil (40) to trocar (38) may be used as well. For example, C-clips, clamps, threading, pins, adhesives, etc. may be employed to couple anvil (40) to trocar (38). In addition, while anvil (40) is described as selectively coupleable to trocar (38), in some versions proximal shaft (42) may include a one-way coupling feature such that anvil (40) cannot be removed from trocar (38) once anvil (40) is attached. Merely exemplary one-way features include barbs, one way snaps, collets, collars, tabs, bands, etc. Of course still other configurations for coupling anvil (40) to trocar (38) will be apparent to one of ordinary skill in the art in view of the teachings herein. For instance, trocar (38) may instead be a hollow shaft and proximal shaft (42) may comprise a sharpened rod that is insertable into the hollow shaft.

Anvil head (48) of the present example comprises a plurality of staple forming pockets (52) formed in a proximal face (50) of anvil head (48). Accordingly, when anvil (40) is in the closed position and staples (66) are driven out of stapling head assembly (20) into staple forming pockets (52), as shown in FIG. 2C, legs (68) of staples (66) are bent to form completed staples. It should be understood that staple forming pockets (52) are merely optional and may be omitted in some versions.

With anvil (40) as a separate component, it should be understood that anvil (40) may be inserted and secured to a portion of tissue (2) prior to being coupled to stapling head assembly (20). By way of example only, anvil (40) may be inserted into and secured to a first tubular portion of tissue (2) while instrument (10) is inserted into and secured to a second tubular portion of tissue (2). For instance, the first tubular portion of tissue (2) may be sutured to or about a portion of anvil (40), and the second tubular portion of tissue (2) may be sutured to or about trocar (38).

As shown in FIG. 2A, anvil (40) is then coupled to trocar (38). Trocar (38) of the present example is shown in a distal most actuated position. Such an extended position for trocar (38) may provide a larger area to which tissue (2) may be coupled prior to attachment of anvil (40). In addition, the extended position of trocar (38) may also provide for easier attachment of anvil (40) to trocar (38). Trocar (38) further includes a tapered distal tip. Such a tip may be capable of piercing through tissue and/or aiding the insertion of anvil (40) on to trocar (38), though the tapered distal tip is merely optional. For instance, in other versions trocar (38) may have a blunt tip. In addition, or in the alternative, trocar (38) may include a magnetic portion (not shown) which may attract anvil (40) towards trocar (38). Of course still further configurations and arrangements for anvil (40) and trocar (38) will be apparent to one of ordinary skill in the art in view of the teachings herein.

When anvil (40) is coupled to trocar (38), the distance between a proximal face of the anvil (40) and a distal face of stapling head assembly (20) defines a gap distance d. Trocar (38) of the present example is translatable longitudinally relative to stapling head assembly (20) via an adjusting knob (98) located at a proximal end of actuator handle assembly (70), as will be described in greater detail below. Accordingly, when anvil (40) is coupled to trocar (38), rotation of adjusting knob (98) enlarges or reduces gap distance d by actuating anvil (40) relative to stapling head assembly (20). For instance, as shown sequentially in FIGS. 2A-2B, anvil (40) is shown actuating proximally relative to actuator handle assembly (70) from an initial, open position to a closed position, thereby reducing the gap distance d and the distance between the two portions of tissue (2) to be joined. Once the gap distance d is brought within a predetermined range, stapling head assembly (20) may be fired, as shown in FIG. 2C, to staple and sever tissue (2) between anvil (40) and stapling head assembly (20). Stapling head assembly (20) is operable to staple and sever tissue (2) by a user pivoting a trigger (74) of actuator handle assembly (70), as will be described in greater detail below.

Figure 5:
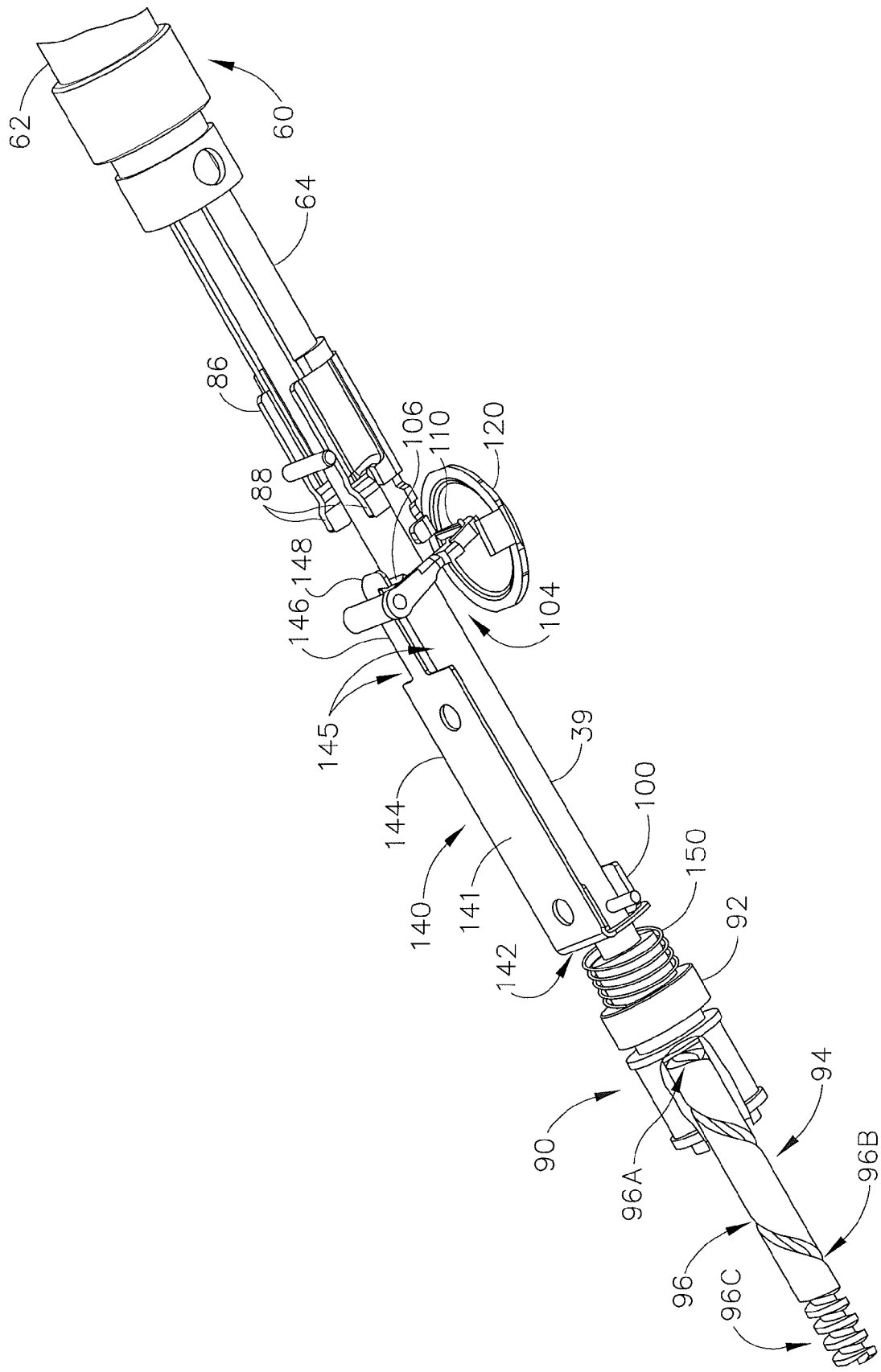
FIG. 5 depicts an enlarged partial perspective view of an exemplary indicator assembly of the surgical instrument of FIG. 1 showing an indicator window and indicator lever.

As noted above, gap distance d corresponds to the distance between anvil (40) and stapling head assembly (20). When instrument (10) is inserted into a patient, this gap distance d may not be easily viewable. Accordingly, a moveable indicator bar (110), shown in FIGS. 5-6, is provided to be visible through an indicator window (120) positioned opposite to trigger (74). Indicator bar (110) is operable to move in response to rotation of adjusting knob (98) such that the position of indicator bar (110) is representative of the gap distance d. As shown in FIG. 6, indicator window (120) further comprises a scale (130) which indicates that the anvil gap is within a desired operating range (e.g., a green colored region or "green zone") and a corresponding staple compression representation at each end of scale (130). By way of example only, as shown in FIG. 6, a first staple image (132) depicts a large staple height while a second staple image (134) depicts a small staple height. Accordingly, a user can view the position of the coupled anvil (40) relative to the stapling head assembly (20) via indicator bar (110) and scale (130). The user may then adjust the positioning of anvil (40) via adjusting knob (98) accordingly.

Referring back to FIGS. 2A-2C, a user sutures a portion of tissue (2) about tubular member (44) such that anvil head (48) is located within a portion of the tissue (2) to be stapled. When tissue (2) is attached to anvil (40), retaining clips (46) and a portion of tubular member (44) protrude out from tissue (2) such that the user may couple anvil (40) to trocar (38). With tissue (2) coupled to trocar (38) and/or another portion of stapling head assembly (20), the user attaches anvil (40) to trocar (38) and actuates anvil (40) proximally towards stapling head assembly (20) to reduce the gap distance d. Once instrument (10) is within the operating range, the user then staples together the ends of tissue (2), thereby forming a substantially contiguous tubular portion of tissue (2).

Anvil (40) may be further constructed in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292,053; U.S. Pat. No. 5,333,773; U.S. Pat. No. 5,350,104; U.S. Pat. No. 5,533,661, the disclosures of which are incorporated by reference herein; and/or in accordance with other configurations as will be apparent to one of ordinary skill in the art in view of the teachings herein.

B. Exemplary Stapling Head Assembly

Stapling head assembly (20) of the present example is coupled to a distal end of shaft assembly (60) and comprises a tubular casing (22) housing a slidable staple driver (24) and a plurality of staples (66) contained within staple pockets (32). Staples (66) and staple pockets (32) are disposed in a circular array about tubular casing (22). In the present example, staples (66) and staple pockets (32) are disposed in a pair of concentric annular rows of staples (66) and staple pockets (32). Staple driver (24) is operable to actuate longitudinally within tubular casing (22) in response to rotation of trigger (74) of actuator handle assembly (70). As shown in FIGS. 2A-2C, staple driver (24) comprises a flared cylindrical member having a trocar opening (26), a central recess (28), and a plurality of members (30) disposed circumferentially about central recess (28) and extending distally relative to shaft assembly (60). Each member (30) is configured to contact and engage a corresponding staple (66) of the plurality of staples (66) within staple pockets (32). Accordingly, when staple driver (24) is actuated distally relative to actuator handle assembly (70), each member (30) drives a corresponding staple (66) out of its staple pocket (32) through a staple aperture (34) formed in a distal end of tubular casing (22). Because each member (30) extends from staple driver (24), the plurality of staples (66) are driven out of stapling head assembly (20) at substantially the same time. When anvil (40) is in the closed position, staples (66) are driven into staple forming pockets (52) to bend legs (68) of the staples (66), thereby stapling the material located between anvil (40) and stapling head assembly (20). FIG. 3 depicts one merely exemplary staple (66) driven by a member (30) into a staple forming pocket (32) of anvil (40) to bend legs (68).

Staple driver (24) further includes a cylindrical knife (36) that is coaxial to trocar opening (26) and inset from staple pockets (32). In the present example, cylindrical knife (36) is disposed within central recess (28) to translate distally with staple driver (24). When anvil (40) is secured to trocar (38), as described above, anvil head (48) provides a surface against which cylindrical knife (36) cuts the material contained between anvil (40) and stapling head assembly (20). In some versions, anvil head (48) may include a recess (not shown) for cylindrical knife (36) to aid in cutting the material (e.g., by providing a cooperative shearing edge). In addition, or in the alternative, anvil head (48) may include one or more opposing cylindrical knives (not shown) offset from cylindrical knife (36) such that a scissor-type cutting action may be provided. Still other configurations will be apparent to one of ordinary skill in the art in view of the teachings herein. Stapling head assembly (20) is thus operable to both staple and cut tissue (2) substantially simultaneously in response to actuation by actuator handle assembly (70).

Of course stapling head assembly (20) may be further constructed in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292, 053; U.S. Pat. No. 5,333,773; U.S. Pat. No. 5,350,104; U.S. Pat. No. 5,533,661, the disclosures of which are incorporated by reference herein; and/or in accordance with other configurations as will be apparent to one of ordinary skill in the art in view of the teachings herein.

As noted previously, staple driver (24) includes a trocar opening (26). Trocar opening (26) is configured to permit trocar (38) to longitudinally slide relative to stapling head assembly (20) and/or shaft assembly (60). As shown in FIGS. 2A-2C, trocar (38) is coupled to a trocar actuator (39) such that trocar (38) can be actuated longitudinally via rotation of rotating knob (98), as will be described in greater detail below in reference to actuator handle assembly (70). In the present example, trocar actuator (39) comprises an elongated, relatively stiff shaft coupled to trocar (38), though this is merely optional. In some versions, actuator (39) may comprise a longitudinally stiff material while permitting lateral bending such that portions of instrument (10) may be selectively bent or curved during use; or instrument (10) may include a preset bent shaft assembly (60). One merely exemplary material is nitinol. When anvil (40) is coupled to trocar (38), trocar (38) and anvil (40) are translatable via actuator (39) to adjust the gap distance d between anvil (40) and stapling head assembly (20). Still further configurations for actuator (39) to longitudinally actuate trocar (38) will be apparent to one of ordinary skill in the art in view of the teachings herein.

C. Exemplary Shaft Assembly

Stapling head assembly (20) and trocar (38) are positioned at a distal end of shaft assembly (60), as shown in FIGS. 2A-2C. Shaft assembly (60) of the present example comprises an outer tubular member (62) and a driver actuator (64). Outer tubular member (62) is coupled to tubular casing (22) of stapling head assembly (20) and to a body (72) of actuator handle assembly (70), thereby providing a mechanical ground for the actuating components therein. The proximal end of driver actuator (64) is coupled to a trigger actuation assembly (84) of actuator handle assembly (70), described below. The distal end of driver actuator (64) is coupled to staple driver (24) such that the rotation of trigger (74) longitudinally actuates staple driver (24). As shown in FIGS. 2A-2C, driver actuator (64) comprises a tubular member having an open longitudinal axis such that actuator (39) coupled to trocar (38) may actuate longitudinally within and relative to driver actuator (64). Of course it should be understood that other components may be disposed within driver actuator (64) as will be apparent to one of ordinary skill in the art in view of the teachings herein.

Shaft assembly (60) may be further constructed in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292,053; U.S. Pat. No. 5,333,773; U.S. Pat. No. 5,350,104; U.S. Pat. No. 5,533, 661, the disclosures of which are incorporated by reference herein; and/or in accordance with other configurations as will be apparent to one of ordinary skill in the art in view of the teachings herein.

D. Exemplary Actuator Handle Assembly

Figure 4A:
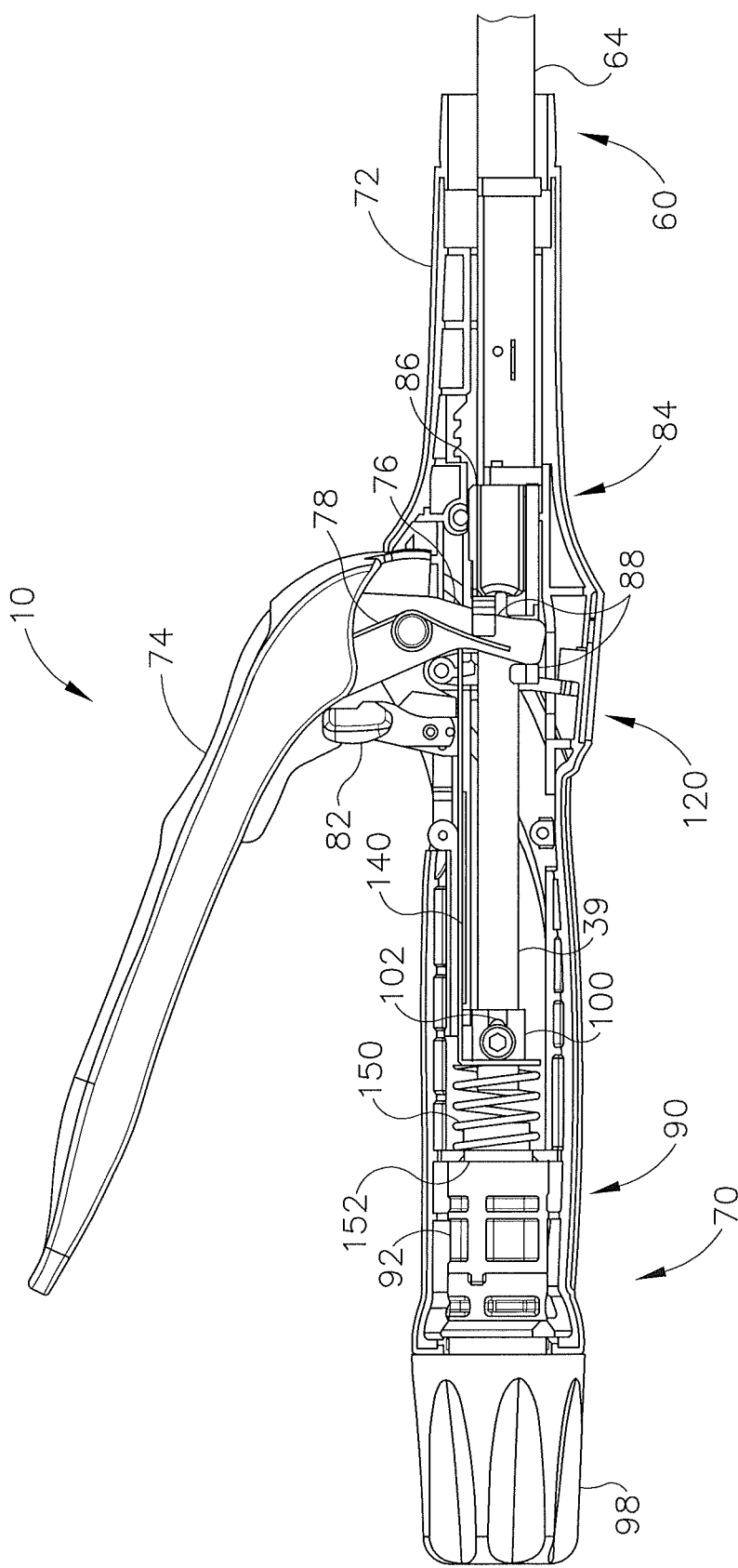
FIG. 4A depicts an enlarged side elevation view of an exemplary actuator handle assembly of the surgical instrument of FIG. 1 with a portion of the body removed, showing a trigger in an unfired position and a lockout feature in a locked position.
Figure 4B:
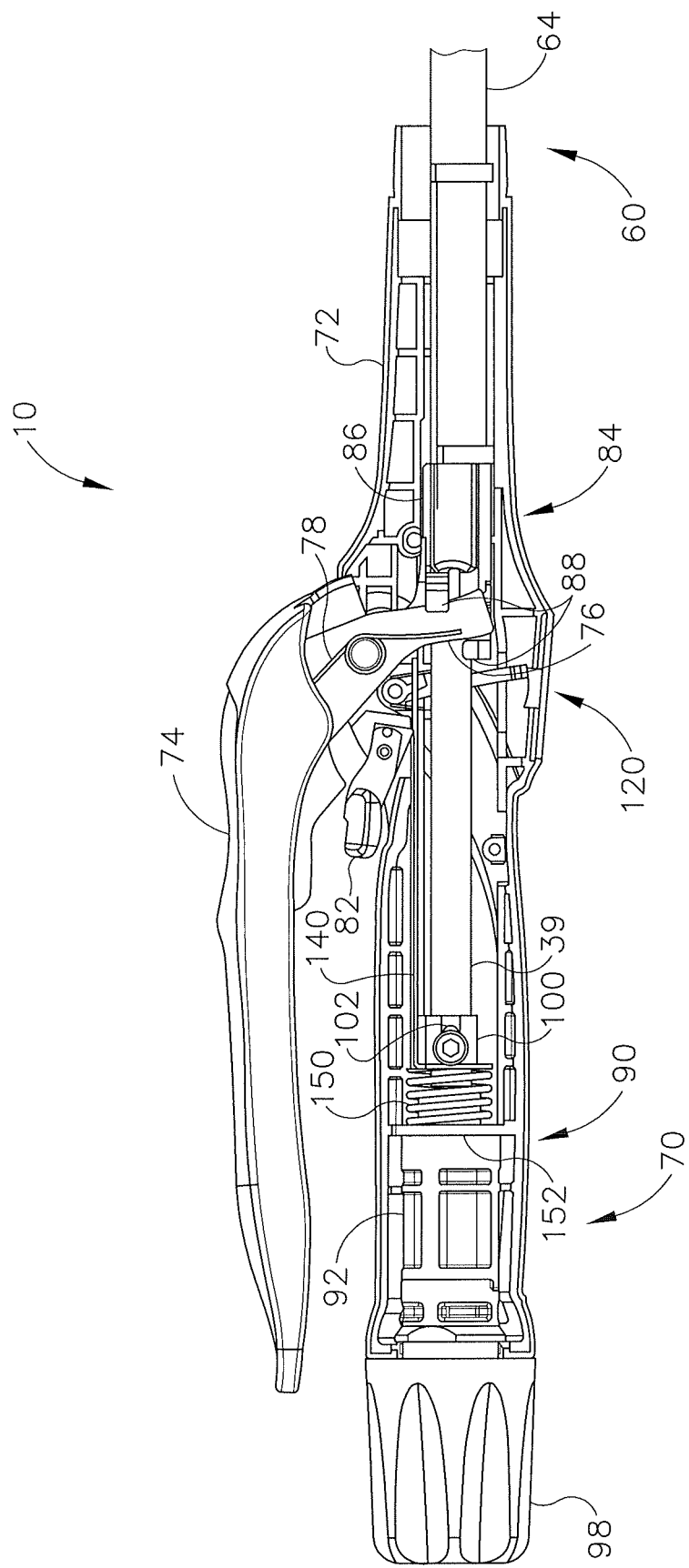
FIG. 4B depicts an enlarged side elevation view of the actuator handle assembly of FIG. 4A, showing the trigger in a fired position and the lockout feature in an unlocked position.

Referring now to FIGS. 4A-5, actuator handle assembly (70) comprises a body (72), a trigger (74), a lockout feature (82), a trigger actuation assembly (84), and a trocar actuation assembly (90). Trigger (74) of the present example is pivotably mounted to body (72) and is coupled to trigger actuation assembly (84) such that rotation of trigger (74) from an unfired position (shown in FIG. 4A) to a fired position (shown in FIG. 4B) actuates driver actuator (64) described above. A spring (78) is coupled to body (72) and trigger (74) to bias trigger (74) towards the unfired position. Lockout feature (82) is a pivotable member that is coupled to body (72). In a first, locked position, lockout feature (82) is pivoted upwards and away from body (72) such that lockout feature (82) engages trigger (74) and mechanically resists actuation of trigger (74) by a user. In a second, unlocked position, such as that shown in FIGS. 1 and 4B, lockout feature (82) is pivoted downward such that trigger (74) may be actuated by the user. Accordingly, with lockout feature (82) in the second position, trigger (74) can engage a trigger actuation assembly (84) to fire instrument (10).

As shown in FIGS. 4A-4B, trigger actuation assembly (84) of the present example comprises a slidable trigger carriage (86) engaged with a proximal end of driver actuator (64). Carriage (86) includes a set of tabs (88) on a proximal end of carriage (86) to retain and engage a pair of trigger arms (76) extending from trigger (74). Accordingly, when trigger (74) is pivoted, carriage (86) is actuated longitudinally and transfers the longitudinal motion to driver actuator (64). In the example shown, carriage (86) is fixedly coupled to the proximal end of driver actuator (64), though this is merely optional. Indeed, in one merely exemplary alternative, carriage (86) may simply abut driver actuator (64) while a distal spring (not shown) biases driver actuator (64) proximally relative to actuator handle assembly (70).

Trigger actuation assembly (84) may be further constructed in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292, 053; U.S. Pat. No. 5,333,773; U.S. Pat. No. 5,350,104; U.S. Pat. No. 5,533,661, the disclosures of which are incorporated by reference herein; and/or in accordance with other configurations as will be apparent to one of ordinary skill in the art in view of the teachings herein.

Body (72) also houses a trocar actuation assembly (90) configured to actuate trocar (38) longitudinally in response to rotation of adjusting knob (98). As best shown in FIGS. 4A-5, trocar actuation assembly (90) of the present example comprises adjusting knob (98), a grooved shank (94), and a sleeve (92). Grooved shank (94) of the present example is located at a distal end of trocar actuator (39), though it should be understood that grooved shank (94) and trocar actuator (39) may alternatively be separate components that engage to transmit longitudinal movement. Adjusting knob (98) is rotatably supported by the proximal end of body (72) and is operable to rotate sleeve (92) that is engaged with grooved shank (94) via an internal tab (not shown). Grooved shank (94) of the present example comprises a continuous groove (96) formed in the outer surface of grooved shank (94). Accordingly, when adjusting knob (98) is rotated, the internal tab rides within groove (96) and grooved shank (94) is longitudinally actuated relative to sleeve (92). Since grooved shank (94) is located at the distal end of trocar actuator (39), rotating adjusting knob (98) in a first direction advances trocar actuator (39) distally relative to actuator handle assembly (70). Accordingly, the gap distance d between anvil (40) and stapling head assembly (20) is increased. By rotating adjusting knob (98) in the opposite direction, trocar actuator (39) is actuated proximally relative to actuator handle assembly (70) to reduce the gap distance d between anvil (40) and stapling head assembly (20). Thus, trocar actuation assembly (90) is operable to actuate trocar (38) in response to rotating adjustment knob (98). Of course other configurations for trocar actuation assembly (90) will be apparent to one of ordinary skill in the art in view of the teachings herein.

Groove (96) of the present example comprises a plurality of different portions (96A, 96B, 96C) that have a varying pitch or number of grooves per axial distance. The present groove (96) is divided into a distal portion (96A), a middle portion (96B) and a proximal portion (96C). As shown in FIG. 5, distal portion (96A) comprises a fine pitch or a high number of grooves over a short axial distance of grooved shank (94) such that a large number of rotations of adjusting knob (98) are required to traverse the short axial distance. Middle portion (96B) comprises a section with comparably coarser pitch or fewer grooves per axial distance such that relatively few rotations are required to traverse a long axial distance. Accordingly, the gap distance d may be quickly reduced through relatively few rotations of adjusting knob (98). Proximal portion (96C) of the present example is substantially similar to distal portion (96A) and comprises a fine pitch or a high number of grooves over a short axial distance of grooved shank (94) such that a large number of rotations are required to traverse the short axial distance. Proximal portion (96C) of the present example is positioned within sleeve (92) when anvil (40) is substantially near to stapling head assembly (20) such that indicator bar (110) moves within indicator window (120) along scale (130) to indicate that the anvil gap is within a desired operating range, as will be described in more detail below. Accordingly, when the tab is within proximal portion (96C) of groove (96), each rotation of adjusting knob (98) may reduce the gap distance d by a small amount to provide for fine tuning.

Trocar actuation assembly (90) may be further constructed in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292,053; U.S. Pat. No. 5,333,773; U.S. Pat. No. 5,350,104; U.S. Pat. No. 5,533,661, the disclosures of which are incorporated by reference herein; and/or in accordance with other configurations as will be apparent to one of ordinary skill in the art in view of the teachings herein.

In the example shown in FIGS. 4A-4B, a U-shaped clip (100) is attached to an intermediate portion of trocar actuator (39) located distally of grooved shank (94). U-shaped clip (100) engages with a portion of body (72) to substantially prevent trocar actuator (39) from rotating about its axis when adjusting knob (98) is rotated. U-shaped clip (100) further includes an elongated slot (102) on each of its opposite sides for receiving an attachment member, such as a screw, bolt, pin, clip, etc., to selectively adjust the longitudinal position of elongated slot (102) of U-shaped clip (100) relative to trocar actuator (39) for purposes of calibrating indicator bar (110) relative to scale (130).

As shown in FIG. 5, actuator handle assembly (70) further includes an indicator bracket (140) configured to engage and pivot an indicator (104). Indicator bracket (140) of the present example is slidable relative to body (72) along a pair of slots formed on body (72). Indicator bracket (140) comprises a rectangular plate (144), an indicator arm (146), and an angled flange (142). Angled flange (142) is formed at the proximal end of rectangular plate (144) and includes an aperture (not shown) to slidable mount onto trocar actuator (39) and/or grooved shank (94). A coil spring (150) is interposed between flange (142) and a boss (152) to bias flange (142) against U-shaped clip (100). Accordingly, when U-shaped clip (100) actuates distally with trocar actuator (39) and/or grooved shank (94), coil spring (150) urges indicator bracket (140) to travel distally with U-shaped clip (100). In addition, U-shaped clip (100) urges indicator bracket (140) proximally relative to boss (152) when trocar actuator (39) and/or grooved shank (94) translate proximally, thereby compressing coil spring (150). Of course, it should be understood that in some versions indicator bracket (140) may be fixedly attached to trocar actuator (39) and/or grooved shank (94).

In the present example, a portion of lockout feature (82) abuts a surface (141) of indicator bracket (140) when indicator bracket (140) is in a longitudinal position that does not correspond to when the anvil gap is within a desired operating range (e.g., a green colored region or "green zone"). When the anvil gap is within a desired operating range (e.g., a green colored region or "green zone"), indicator bracket (140) narrows to provide a pair of gaps (145) on either side of an indicator arm (146) that permits lockout feature (82) to pivot, thereby releasing trigger (74). Accordingly, lockout feature (82) and indicator bracket (140) can substantially prevent a user from releasing and operating trigger (74) until anvil (40) is in a predetermined operating range. Of course it should be understood that lockout feature (82) may be omitted entirely in some versions.

This operating range may be visually communicated to the user via an indicator bar (110) of an indicator (104) shown against a scale (130), described briefly above. At the distal end of indicator bracket (140) is a distally projecting indicator arm (146) which terminates at a laterally projecting finger (148) for controlling the movement of indicator (104). Indicator arm (146) and finger (148), best shown in FIG. 5, are configured to engage a tab (106) of indicator (104) such that indicator (104) is pivoted when indicator bracket (140) is actuated longitudinally. In the present example, indicator (104) is pivotably coupled to body (72) at a first end of indicator (104), though this is merely optional and other pivot points for indicator (104) will be apparent to one of ordinary skill in the art in view of the teachings herein. An indicator bar (110) is positioned on the second end of indicator (104) such that indicator bar (110) moves in response to the actuation of indicator bracket (140). Accordingly, as discussed above, indicator bar (110) is displayed through an indicator window (120) against a scale (130) (shown in FIG. 6) to show the relative gap distance d between anvil (40) and stapling head assembly (20).

Of course indicator bracket (140), indicator (104), and/or actuator handle assembly (70) may be further constructed in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292,053; U.S. Pat. No. 5,333,773; U.S. Pat. No. 5,350,104; U.S. Pat. No. 5,533,661, the disclosures of which are incorporated by reference herein; and/or in accordance with other configurations as will be apparent to one of ordinary skill in the art in view of the teachings herein.

II. Exemplary Staple and Pledget Assemblies

In an anastomosis, two layers of severed tissue (2) are stapled together utilizing, for example, a circular stapler such as instrument (10), described above. As described below, staple (66) may be used with a pledget to increase a pressure zone of crown (200) of staple (66); and to increase an effective width of staple legs (68) after staple legs (68) are bent by staple forming pockets (52) to capture tissue (2), as described above. The pledget has a length that is greater than a length of crown (200) to increase an effective length of crown (200) after staple legs (68) are bent by staple forming pockets (52) to capture tissue (2), as described above. Such an increased footprint of staple (66) via an increased staple leg width and/or an increased crown length that occurs after staple (66) has captured severed tissue (2) may increase hemostasis at the severed tissue site and/or increase the structural integrity of the anastomosis. The increase in the effective footprint may spread out and distribute forces that staple (66) applies to the anastomosis to assist with the increase in the structural integrity of the anastomosis.

Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the references cited herein will be apparent to those of ordinary skill in the art. It should also be understood that the below teachings are not limited to instrument (10) or devices taught in the references cited herein. The below teachings may be readily applied to various other kinds of instruments, including but not limited to linear staplers. Various other suitable devices and settings in which the below teachings may be applied will be apparent to those of ordinary skill in the art in view of the teachings herein.

A. Exemplary Staple with Tilting Pledget

Figure 7A:
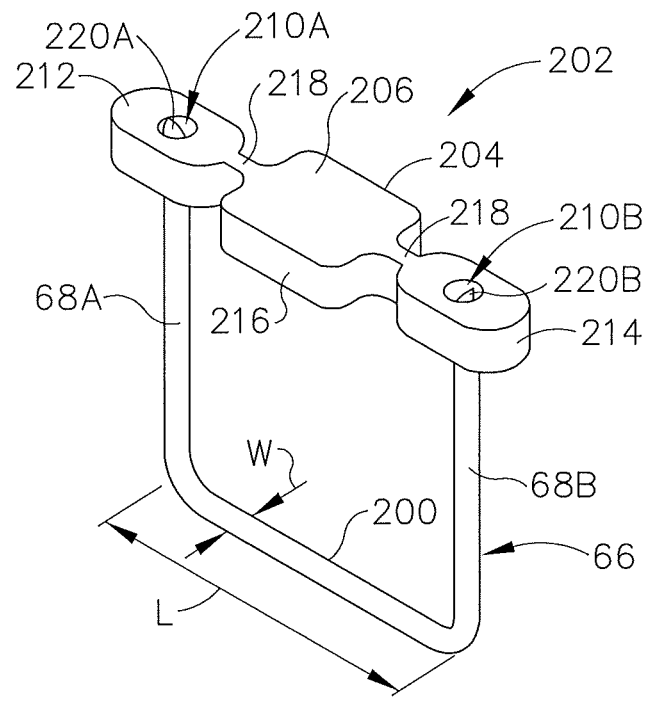
FIG. 7A depicts a perspective view of an exemplary staple in a first position with respect to an exemplary pledget to form an exemplary staple and pledget assembly.

FIGS. 7A-9D show a first exemplary staple and pledget assembly (202), which includes staple (66) and pledget (204). Pledget (204) includes upper surface (206), lower surface (208), and a pair of channels (210A, 210B) disposed between upper surface (206) and lower surface (208). Channels (210A, 210B) are disposed an opposite ends of pledget (204) and are sized and shaped to receive legs (68A, 68B) of staple (66) in an initial, unbent first position, as shown in FIG. 7A. Upper surface (206) may be angled and/or curved to promote tilting of pledget (204) and deflection of staple (66) as described below.

Figure 8:
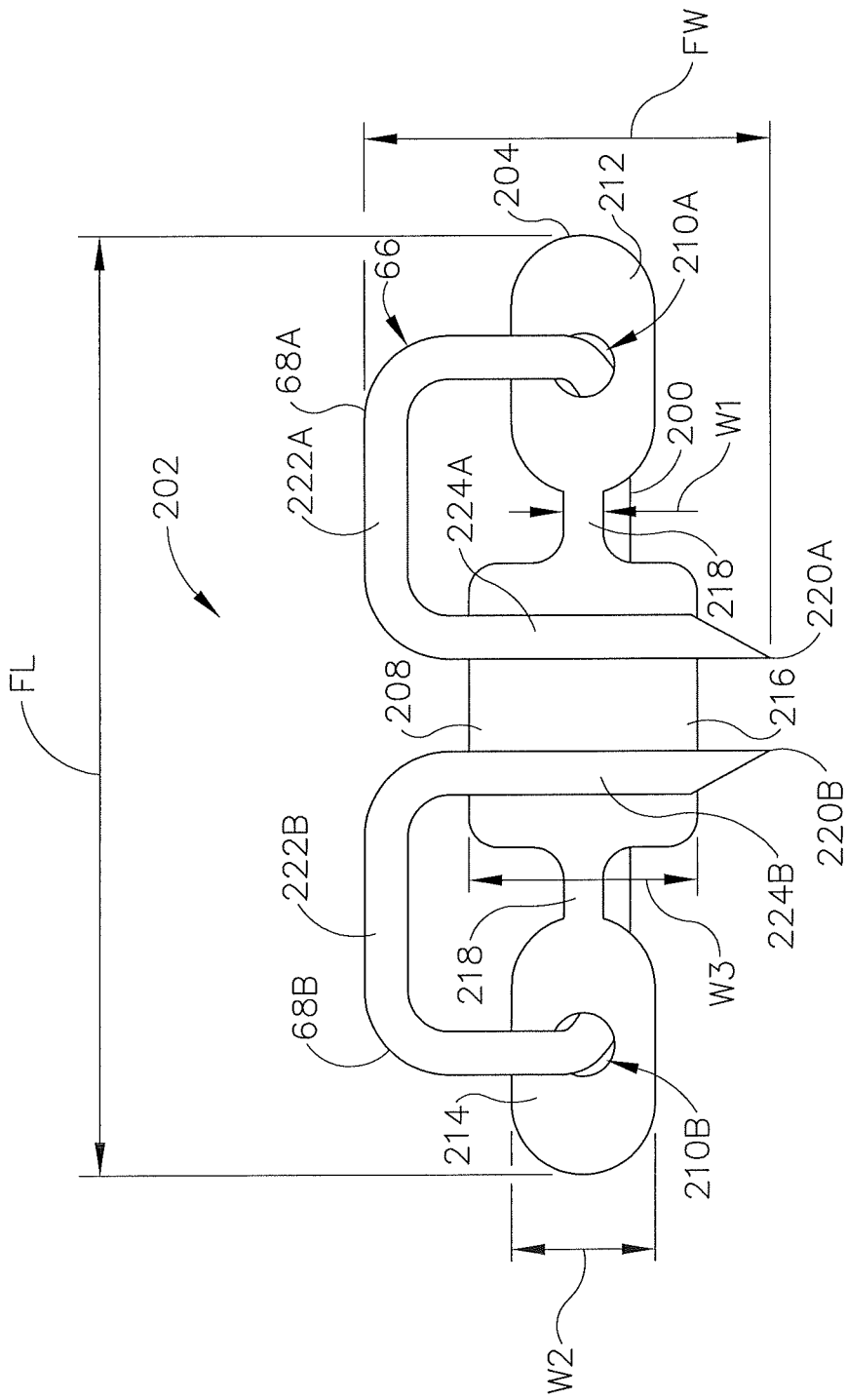
FIG. 8 depicts a top plan view of the exemplary staple and pledget assembly of FIG. 7D.

Pledget (204) includes end portions (212, 214) and intermediate portion (216) disposed between end portions (212, 214) and attached to end portions (212, 214) via bridge portions (218). FIG. 8 shows that bridge portions (218) have width W1 that is less than width W2 of end portions (212, 214). Width W2 is less than width W3 of intermediate portion (216). While end portions (212, 214) comprise a generally oval cross-sectional shape and bridge portions (218) and intermediate portion (216) comprise a generally square or rectangular cross-section shape, other cross-sectional shapes are possible as will be apparent to one of ordinary skill in the art in view of the teachings herein. Further, pledget (204) may include interference ribs (not shown) along its perimeter to assist with maintaining pledget (204) within staple pocket (32) prior to driving staple (66) toward staple forming pocket (52) of anvil (40).

Pledget (204) may comprise a flexible bioabsorbable material or an absorbable plastic such as, for example, Polyglycolic acid ("PGA") marketed under the trade name VICRYL, Polylactic acid ("PLA" or "PLLA"), Polydioxanone ("PDS"), polycaprolactone ("PCL"), polyhydroxyalkanoate ("PHA"), poliglecaprone 25 sold under trademark MONOCRYL ("PGCL), or various composite mixes of the above as will be apparent to those of ordinary skill in the art in view of the teachings herein. In addition or in the alternative, pledget (204) may comprise absorbable materials as disclosed in U.S. Patent App. Publ. No. 2012/0080335, entitled "Compressible Fastener Cartridge," published Apr. 5, 2012, now U.S. Pat. No. 8,740,037, issued Jun. 3, 2014; and/or materials disclosed in U.S. Patent App. Publ. No. 2011/0060363, entitled "Surgical Staples Having Compressible or Crushable Member for Securing Tissue Therein and Stapling Instruments for Deploying the Same," filed Mar. 10, 2011, the disclosures of which are incorporated by reference herein. Other suitable materials that may be used to form pledget (204) will be apparent to those of ordinary skill in the art in view of the teachings herein.

Prior to the driving of staples (66) into anvil (40) as described above, pledget (204) is seated in the deck of tubular casing (22). In use and in a first position, as shown in FIGS. 7A and 9A, distal ends (220A, 220B) of staple legs (68A, 68B) are advanced through staple pockets (32) of tubular casing (22) via advancement of staple driver (24), as described above. Distal ends (220A, 220B) are received within respective channels (210A, 210B) of pledget (204). Distal ends (220A, 220B) advance toward stapling forming pockets (52) of anvil (40).

Figure 7B:
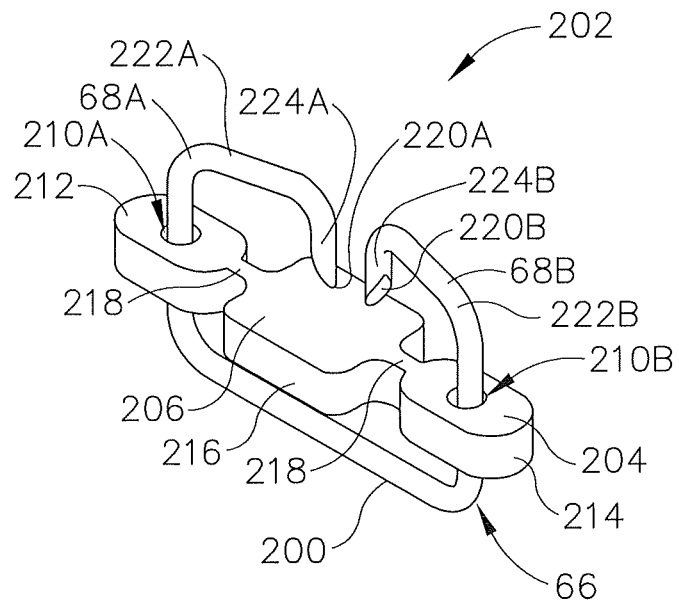
FIG. 7B depicts a perspective view of the exemplary staple and pledget assembly of FIG. 7A in a second position.

As staple driver (24) continues to drive staple (66) into anvil (40), staple (66) eventually reaches a second position, as shown in FIGS. 7B and 9B. With staple (66) in the second position, distal ends (220A, 220B) are bent inwardly toward one another by stapling forming pockets (52), which create first bent portions (222A, 222B) of each staple leg (68A, 68B) that are substantially parallel to a longitudinal axis of crown (200), and second bent portions (224A, 224B) that are substantially perpendicular to first bent portion (222A, 222B). Distal ends (220A, 220B) are bent until disposed on upper surface (206) of pledget (204).

Figure 7C:
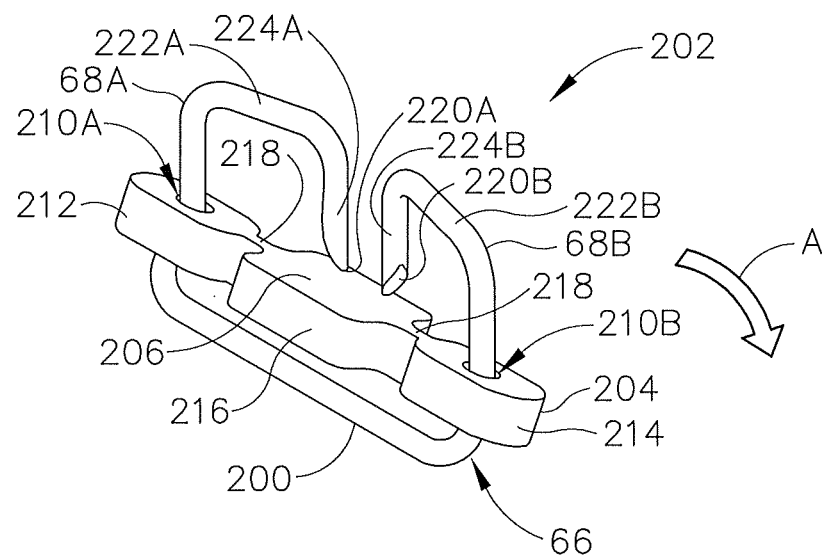
FIG. 7C depicts a perspective view of the exemplary staple and pledget assembly of FIG. 7A in a third position.

As staple driver (24) continues to drive staple (66) into anvil (40), staple (66) eventually reaches a third position, as shown in FIGS. 7C and 9C. With staple (66) in the third position, a load from distal ends (220A, 220B) on upper surface (206) causes pledget (204) to tilt in a first direction of arrow (A) and rotate about a longitudinal axis of pledget (204). Distal ends (220A, 220B) deflect to advance in the direction of arrow (A) along upper surface (206) of pledget (204). As shown in FIG. 9C, as pledget (204) beings to tilt, tissue (2) captured between pledget (204), staple (66), and anvil (40) begins to twist and compress between pledget (204) and first bent portions (222A, 222B). As noted above, providing an incline or curve on upper surface (206) may promote the deflection of distal ends (220A, 220B) and/or tilting of pledget (204) at this stage.

Figure 7D:
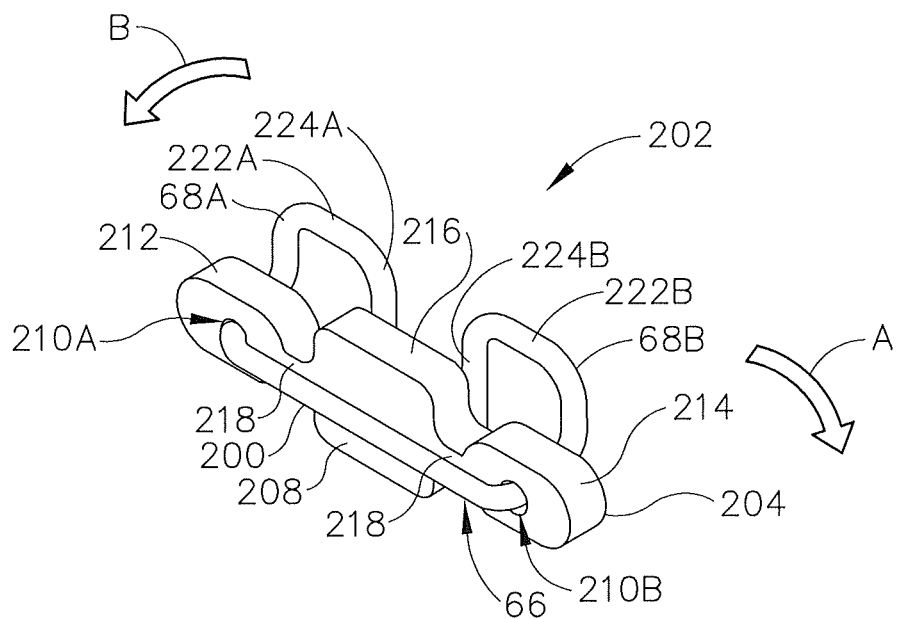
FIG. 7D depicts a perspective view of the exemplary staple and pledget assembly of FIG. 7A in a fourth position.

As staple driver (24) continues to drive staple (66) into anvil (40), staple (66) eventually reaches a fourth position, as shown in FIGS. 7D, 8, and 9D. With staple (66) in the fourth position, as distal ends (220A, 220B) have advanced in the direction of arrow (A) along upper surface (206) to advance past a perimeter of pledget (204), first bent portions (222A, 222B) of staple (66) have deflected to be bent in the opposite second direction of arrow (B). In this final position, as shown in FIG. 8, pledget (204) has an overall width defined by footprint width (FW), measuring a distance between first bent portions (222A, 222B) and distal ends (220A, 220B) of staple (66). Through the ability to fold over laterally about pledget (204), as described above, staple (66) has a width that is increased relative to the width of a similar staple (66) that lacks pledget (204). In some instances, this width is increased by about 5 to 10 times relative to the width of a similar staple (66) that lacks pledget (204). In a final position, distal ends (220A, 220B) are laterally offset or spaced away from a plane in which crown (200) is disposed. In particular, distal ends (220A, 220B) are laterally offset or spaced away from a plane passing through crown (200) and pledget (204). As an interior surface of crown (200) is further covered by pledget (204) in the fourth, final position, a pressure area associated with crown (200) against tissue (2) is increased relative to the pressure area of a similar staple (66) that lacks pledget (204). In some instances, this pressure area is increased by about 3 to 5 times relative to the pressure area of a similar staple (66) that lacks pledget (204).

Staple and pledget assembly (202), with the combination of the tiltable pledget (204) and deflectable staple legs (68) as described above, create footprint width (FW) and footprint length (FL) measured between ends of end portions (212, 214) of pledget (204) as shown in FIG. 8. Footprint width (FW) is greater than width (W) of crown (200) of staple (66) shown in FIG. 7A, and footprint length (FL) is greater than length (L) of crown (200) of staple (66) shown in FIG. 7A. The combination of a wider footprint width (FW) and a longer footprint length (FL) may provide a significantly greater pressure footprint than would otherwise be provided by a conventional formed staple. It should also be understood that the greater footprint size may reduce the risk that the deployed/formed staple and pledget assembly (202) would unintentionally tear through the stapled tissue. In other words, the deployed/formed staple and pledget assembly (202) may spread out stress along a greater surface area of tissue, and thereby avoid tearing through the tissue in response to significant stress; whereas a conventional staple lacking pledget (204) might tend to tear through tissue under the same stress in a manner similar to a wire cheese cutter since the stress would be applied along a relatively thin line. Tissue can thus bear relatively greater forces when they are imposed by the deployed/formed staple and pledget assembly (202).

Footprint width (FW) and footprint length (FL) together create a three-dimensional pressure profile of deployed/formed staple and pledget assembly (202) that allows for application of pressure along a plane that is transverse to a plane along which staple (66) is driven. Such a three-dimensional pressure profile of staple (66) after staple (66) has captured severed layers (2A, 2B) of tissue (2) and pledget (204) has twisted and clamped against severed tissue (2) may increase hemostasis at the severed tissue site and/or increase the structural integrity of the anastomosis as described above. The deployed/formed staple and pledget assembly (202) may thus provide significantly greater hemostasis and/or significantly greater structural integrity for an anastomosis than might otherwise be achieved using a conventional formed staple.

It should also be understood that the tilted configuration of deployed/formed staple and pledget assembly (202) may tilt the tissue adjacent to a cut line. In instances where staple and pledget assembly (202) is used in a circular stapler to form an end-to-end anastomosis of bodily lumens (e.g., within the gastro-intestinal tract), this may result in an anastomosis inner edge that is tilted downwardly, away from the natural flow of contents through the bodily lumens (e.g., bowel contents). Such an anastomosis configuration may thus facilitate the flow of contents through the anastomosed path, or at least produce less impedance to such flow than might otherwise result from using a conventional staple configuration.

B. Exemplary Staple and Pledget Assembly Providing Asymmetric Formed Staple Legs FIGS. 10A-12 show another exemplary staple and pledget assembly (302), which includes staple (66) and pledget (304). Pledget (304) includes upper surface (306), lower surface (308), and a pair of channels (310A, 310B) disposed between upper surface (306) and lower surface (308). Channels (310A, 310B) are disposed an opposite ends of pledget (304) and are sized and shaped to receive legs (68A, 68B) of staple (66) in an initial, unbent first position, as shown in FIG. 10A. Upper surface (306) comprises angled, ramped surfaces as shown in FIG. 12 to promote deflection of legs (68A, 68B) of staple (66) as described below.

Pledget (304) includes end portions (312, 314) and intermediate portion (316), which is disposed between end portions (312, 314) and attached to end portions (312, 314) via bridge portions (318). Pledget (304) is similar to pledget (204) other than as described above and as described below with respect to intermediate portion (316). Intermediate portion (316) of pledget (304) includes a pair of diagonally opposed outrigger projections (319A, 319B) disposed on opposite sides of intermediate portion (316). While a generally circular cross-sectional shape is shown for projections (319A, 319B), other suitable shapes are possible as will be apparent to those of ordinary skill in the art in view of the teachings herein.

Prior to the driving of staples (66) into anvil (40) as described above, pledget (304) is seated in the deck of tubular casing (22). In use and in a first position, as shown in FIG. 10A, distal ends (220A, 220B) of staple legs (68A, 68B) are advanced through staple pockets (32) of tubular casing (22) via advancement of staple driver (24), as described above. Distal ends (220A, 220B) are received within respective channels (310A, 310B) of pledget (304). Distal ends (220A, 220B) advance toward stapling forming pockets (52) of anvil (40).

As staple driver (24) continues to drive staple (66) into anvil (40), staple (66) eventually reaches a second position, as shown in FIG. 10B. With staple (66) in the second position, distal ends (220A, 220B) are bent inwardly by stapling forming pockets (52), which create first bent portions (222A, 222B) of each staple leg (68A, 68B) that are substantially parallel to a longitudinal axis of crown (200), and second bent portions (224A, 224B) that are substantially perpendicular to first bent portion (222A, 222B). Distal ends (220A, 220B) are bent until disposed on upper surface (206) of pledget (204). In this second position, distal end (220A) is disposed on point (P1) on upper surface (306) of pledget (304) and distal end (220B) is disposed on point (P2) on upper surface (306) of pledget (304).

As staple driver (24) continues to drive staple (66) into anvil (40), staple (66) eventually reaches a third position, as shown in FIG. 10C. With staple (66) in the third position, distal end (220A) deflects to advance in the direction of arrow (B) along upper surface (306) of pledget (304), and distal end (220B) deflects to advance in the opposite direction of arrow (A) along upper surface (306) of pledget (304). Severed tissue (2) is clamped and captured between first bent portions (222A, 222B) of staple (66) and pledget (304).

As staple driver (24) continues to drive staple (66) into anvil (40), staple (66) eventually reaches a fourth position, as shown in FIGS. 11 and 12. With staple (66) in the fourth position, as distal ends (220A, 220B) have respectively advanced in the direction of arrows (B, A) along upper surface (306), first bent portions (222A, 222B) of staple (66) have deflected to be bent in the respective opposite directions of arrows (B, A). Thus, as distal end (220A) deflects in the direction of arrow (B), first bent portion (222A) deflects in the opposite direction of arrow (A). And as distal end (220B) deflects in the direction of arrow (A), first bent portion (222B) deflects in the opposite direction of arrow (B) to arrive in the position shown in FIGS. 11-12. Severed tissue (2) is clamped and captured between first bent portions (222A, 222B) of staple (66) and pledget (304), and severed tissue (2) is clamped and captured between distal ends (220A, 220B) and projections (319A, 319B), assisting to create an increased pressure zone against clamped tissue as described below.

In this final position, bent/formed staple legs (68A, 68B) together define a footprint width (FFW), as shown in FIG. 11. Footprint width (FFW) is greater than width (W) of crown (200) of staple (66) shown in FIG. 10A. Footprint width (FFW) is also greater than width of a conventionally formed staple, which in some cases may be approximately equal to or insignificantly greater than width (W) of crown (200). It should also be noted that pledget (304) has an overall length defined by footprint length (FFL), measured between the outer ends of end portions (312, 314) of pledget (204) as shown in FIG. 11. Footprint length (FFL) is greater than length (L) of crown (200) of staple (66) shown in FIG. 10A. The combination of a wider footprint width (FFW) and a longer footprint length (FFL) may provide a significantly greater pressure footprint than would otherwise be provided by a conventional formed staple. In some instances the increased footprint of pressure is increased by about 5 times relative to a similar staple (66) lacking pledget (304). It should also be understood that the greater footprint size may reduce the risk that the deployed/formed staple and pledget assembly (302) would unintentionally tear through the stapled tissue. In other words, the deployed/formed staple and pledget assembly (302) may spread out stress along a greater surface area of tissue, and thereby avoid tearing through the tissue in response to significant stress; whereas a conventional staple lacking pledget (304) might tend to tear through tissue under the same stress in a manner similar to a wire cheese cutter since the stress would be applied along a relatively thin line. Tissue can thus bear relatively greater forces when they are imposed by the deployed/formed staple and pledget assembly (302).

In addition, it should be noted that footprint width (FFW) and footprint length (FFL) together create a three-dimensional pressure profile of deployed/formed staple and pledget assembly (302) that allows for application of pressure along a plane that is transverse to a plane along which staple (66) is driven. Such a three-dimensional pressure profile of staple (66) after staple (66) has captured severed layers (2A, 2B) of tissue (2) and pledget (304) has clamped against severed tissue (2) may increase hemostasis at the severed tissue site and/or increase the structural integrity of the anastomosis as described above. The deployed/formed staple and pledget assembly (302) may thus provide significantly greater hemostasis and/or significantly greater structural integrity for an anastomosis than might otherwise be achieved using a conventional formed staple.

III. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. A stapler apparatus for stapling a tissue, the apparatus comprising:
    (a) an anvil having an anvil head, wherein the anvil head defines a staple-forming pocket;
    (b) a stapling head assembly operable to drive a staple toward the staple-forming pocket; and
    (c) a staple and pledget assembly coupled with the stapling head assembly, wherein the staple and pledget assembly comprises:

(i) a staple having a pair of legs and a crown, wherein the crown has a crown width and a crown length and is configured to apply a first pressure to the tissue along a first plane, wherein the pair of legs are disposed substantially perpendicular to the crown in a first position, wherein the pair of legs is operable to advance against the pocket in the anvil head to form a staple with bent legs, and (ii) a pledget configured to receive the pair of legs of the staple, wherein the pledget is configured to deflect portions of the pair of legs of the staple away from a longitudinal axis of the crown such that the pledget and the staple define a formed staple configured to apply a second pressure to the tissue along a second plane transverse to the first plane, wherein the first and second planes are arranged to form a three-dimensional pressure profile.

2. The apparatus of claim 1, wherein the pledget comprises a pair of channels configured to receive distal ends of the pair of legs of the staple.

3. The apparatus of claim 1, wherein the distal ends of the pair of legs are configured to be bent by the pocket in the anvil head to form a pair of first bent portions and a pair of second bent portions, wherein each first bent portion is substantially parallel to a longitudinal axis of the crown of the staple, and wherein each second bent portion is substantially perpendicular to a respective first bent portion.

4. The apparatus of claim 3, wherein the second bent portions comprise the distal ends of the pair of legs, and wherein the distal ends of the pair of legs are configured to be disposed against an upper surface of the pledget.

5. The apparatus of claim 4, wherein the pledget is configured to tilt relative to the staple in response to the distal ends of the pair of legs bearing against an upper surface of the pledget.

6. The apparatus of claim 1, wherein the distal ends of the pair of legs are configured to be bent by the pocket in the anvil head to form a pair of first bent portions and a pair of second bent portions, wherein the distal ends of the pair of legs are configured to advance to a position disposed past a first side of the crown, and the first bent portions are configured to deflect to a position disposed past a second, opposite side of the crown.

7. The apparatus of claim 1, wherein the distal ends of the pair of legs are configured to be bent by the pocket in the anvil head to form a pair of first bent portions and a pair of second bent portions, wherein the formed staple is configured to form a width footprint measurable as a distance between the first bent portions and the distal ends of the pair of legs, wherein the width footprint is greater than the crown width.

8. The apparatus of claim 1, wherein the distal end of a first one of the legs is configured to advance in the first direction, wherein the distal end of a second one of the legs is configured to advance in a second direction, wherein the second direction is opposite the first direction.

9. The apparatus of claim 8, wherein the pledget is configured to deflect the distal end of the first one of the legs in the first direction, wherein the pledget is further configured to deflect the distal end of the second one of the legs in the second direction.

10. The apparatus of claim 1, wherein each leg of the formed staple comprises a first bent portion and a second bent portion, wherein the formed staple is configured to form a width footprint measurable as a distance between the first bent portion and the second bent portion, wherein the width footprint is greater than the crown width.

11. The apparatus of claim 1, wherein the pledget comprises a pair of end portions and an intermediate portion disposed between the pair of end portions, wherein the pair of end portions comprise channels sized and shaped to receive distal ends of the pair of legs of the staple, wherein a width of the intermediate portion is greater than a width of each of the end portions, and wherein the intermediate portion comprises at least one projection.

12. The apparatus of claim 1, wherein the pledget comprises a bioabsorbable material.

13. The apparatus of claim 1, wherein the anvil comprises a plurality of staple-forming pockets arranged in an annular array, wherein the stapling head assembly includes a plurality of staples arranged in an annular array.

14. The apparatus of claim 1, wherein a length of the pledget is greater than the crown length.

15. The apparatus of claim 1, wherein distal ends of the pair of legs of the formed staple are laterally offset from the longitudinal axis of the crown of the staple, wherein the each of the distal ends are either both disposed on a first side of the crown or respectively disposed on a first and second side of the crown.

16. A method of forming a staple with bent legs using a stapler apparatus, wherein the apparatus includes a staple and pledget assembly and a staple head operable to drive staples toward an anvil head, wherein a staple of the staple and pledget assembly has a pair of legs disposed substantially perpendicular to a crown of the staple in a first position, wherein distal ends of the pair of legs are configured for receipt within a pair of channels defined in opposing end portions of the pledget, wherein the pair of legs is operable to advance against a respective pocket in the anvil head to form the staple with bent legs, the method comprising:

(a) advancing the distal ends toward the respective pockets in the anvil head;

(b) bending the distal ends of the pair of legs via the respective pockets to form first bent portions and second bent portions, the second bent portions including the distal ends;

(d) advancing the second bent portions toward an upper surface of the pledget;

(e) tilting the pledget in a first angular direction to rotate about a longitudinal axis of the pledget while advancing the second bent portions toward the pledget; and (f) deflecting the first bent portions while tilting the pledget in the first angular direction to create a footprint in which the distal ends are laterally spaced away from a plane passing through the pledget and the crown.

17. The method of claim 16, further comprising advancing the distal ends to a position disposed past a first side of the crown and deflecting the first bent portions to a position disposed past a second, opposite side of the crown while tilting the pledget in the first angular direction.

18. The method of claim 16, further comprising advancing one of the distal ends in a first linear direction, and advancing the other of the distal ends in a second linear direction opposite the first direction.

19. The method of claim 16, further comprising deflecting portions of each staple leg in a second angular direction, wherein the second angular direction is opposite to the first angular direction.

20. A circular stapler apparatus for stapling a tissue, the apparatus comprising:

(a) an anvil having an anvil head, wherein the anvil head defines a staple-forming pocket;

(b) a stapling head assembly operable to drive a staple toward the staple-forming pocket; and (c) a staple and pledget assembly coupled with the stapling head assembly, wherein the staple and pledget assembly comprises:
  (i) a staple having a pair of legs and a crown, wherein the crown is configured to apply a first pressure to the tissue along a first plane, wherein the pair of legs are disposed substantially perpendicular to the crown in a first position, wherein the pair of legs is operable to advance against the pocket in the anvil head to form a staple with bent legs, and
  (ii) a pledget configured to receive the pair of legs of the staple, wherein the pledget is configured to deflect portions of the pair of legs of the staple in opposite directions away from a longitudinal axis of the crown such that the pledget and the staple define a formed staple configured to apply a second pressure to the tissue along a second plane transverse to the first plane, wherein the first and second planes are arranged to form a three-dimensional pressure profile.

* * * * *